US00PP18769P3

(12) United States Plant Patent
Takamura et al.

(10) Patent No.: US PP18,769 P3
(45) Date of Patent: Apr. 29, 2008

(54) ***VERBENA* PLANT NAMED 'SURVIVASAMO'**

(50) Latin Name: *Verbena hybrida*
Varietal Denomination: Sunvivasamo

(75) Inventors: Naoto Takamura, Omihachiman (JP); Tomoya Misato, Omihachiman (JP)

(73) Assignee: Suntory Flowers Limited, Tokyo (JP)

( * ) Notice: Subject to any disclaimer, the term of this patent is extended or adjusted under 35 U.S.C. 154(b) by 689 days.

(21) Appl. No.: 10/810,335

(22) Filed: Mar. 26, 2004

(65) Prior Publication Data

US 2005/0216991 P1 Sep. 29, 2005

(51) Int. Cl.
*A01H 5/00* (2006.01)

(52) U.S. Cl. ..... Plt./308
(58) Field of Classification Search ..... Plt./308
See application file for complete search history.

(56) References Cited

FOREIGN PATENT DOCUMENTS

JP RBR 7396 9/1999

JP PBR 9554 11/2001

OTHER PUBLICATIONS

Explanation for IDS Documents.

Jackson & Perkins wholesale, Inc., USA, "The 2004 Suntory Collection" Published 2003.

Pineae Greenhouses, Inc., USA, "Pineae Peak Performers featuring the 2004 Suntory COLLECTION" Published 2003.

*Primary Examiner*—Wendy C. Haas
*Assistant Examiner*—Georgia Helmer
(74) *Attorney, Agent, or Firm*—Christie, Parker & Hale, LLP

(57) ABSTRACT

Disclosed herein is a new and distinct variety of *Verbena* planting having a semi-erect growth habit. The new *Verbena* plant has abundant branching, the whole plant remaining in bloom for a considerable period of time. The flowers are formed in profusion in a spike and the petals display a deep purplish pink color. The blooming period is from April to November, and the flowering duration is long. The plant exhibits high tolerance to heat, high resistance to rain, pests and disease, particularly powdery mildew.

2 Drawing Sheets

Botanical classification: *Verbena hybrida.*
Varietal denomination: 'Sunvivasamo'.

BACKGROUND OF THE VARIETY

The present invention relates to a new variety of *Verbena* plant, named 'Sunvivasamo', which originated from open-pollination of a *Verbena* hybrid variety called '142-13' (unpatented).

The *Verbena* is a very popular plant and is used for flower bedding and potting in the summer season. There are only a few varieties of the *Verbena* plant that have abundant branching, many deep purplish pink flowers in a spike, and a high resistance to heat, rain, and disease. Accordingly, this invention was aimed at obtaining a new *Verbena* variety having a decumbent growth habit, much branching, many flowers in a spike, high tolerance to heat and rain, and resistance to disease and pests.

The parent variety '142-13' used in the open-pollination of 'Sunvivasamo' is a strain of our breeding lines. The plant height of '142-13' is lower than 'Sunvivasamo', and the petal color of '143-13' is purplish pink, which is lighter than that of 'Sunvivasamo' (near R.H.S. 68A).

In October 1997, 2000 seedlings were obtained from the natural crosses of *Verbena* variety called '142-13', and were grown in a controlled environment at Yokaichi-shi, Shiga-ken, Japan. These seedlings were grown in pots in glass-houses for evaluation. One seedling was selected in view of its growth habit and flower color in October 2001. That seedling was propagated by cutting and a trail was carried out by flower potting and bedding from May to November 2002. The botanical characteristics of that plant were then examined, using similar varieties 'Sunvivasa' (unpatented) and 'Sunvivapi' (unpatented) for comparison. As a result, it was concluded that this *Verbena* plant is distinguishable from any other variety, whose existence is known to us, and is uniform and stable in its characteristics. The new variety of *Verbena* plant was named 'Sunvivasamo'.

In the following description, the color-coding is in accordance with the Horticultural Colour Chart of The Royal Horticultural Society, London, England (R.H.S.).

SUMMARY OF THE VARIETY

This new variety is unlike any commercially available *Verbena* known to us as evidenced by the following unique combinations of characteristics.

1. Semi-erect growth habit with abundant branching.
2. Plentiful number of flowers in a spike, having a great profusion of blooms with the entire plant remaining in bloom for a considerable period of time.
3. Long flowering duration.
4. The petal color is deep purplish pink (near R.H.S. 68A).
5. The plant has a high resistance to rain, heat, disease and pests.

The new variety 'Sunvivasamo' differs from the similar variety 'Sunvivasa' in the following points.

1. The internode length of 'Sunvivasamo' is shorter than that of 'Sunvivasa'.
2. The floret length of 'Sunvivasamo' is shorter than that of 'Sunvivasa'.
3. The petal color of 'Sunvivasamo' is deep purplish pink (near R.H.S. 68A), while that of 'Sunvivasa' is light purplish pink (near R.H.S. 54D).
4. The number of flowers per spike of 'Sunvivasmo' is more than that of 'Sunvivasa'.

The new variety 'Sunvivasamo' differs from the similar variety 'Sunvivapi' in the following points.

1. The internode length of 'Sunvivasamo' is shorter than that of 'Sunvivapi'.
2. The leaf of 'Sunvivasamo' is smaller than that of 'Sunvivapi'.
3. The leaf shape of 'Sunvivasamo' is oblong, having serrate margin, while that of 'Sunvivapi' is hastate, having create margin.
4. The floret length of 'Sunvivasamo' is taller than that of 'Sunvivapi'.
5. The petal color of 'Sunvivasamo' is deep purplish pink (near R.H.S. 68A, while that of 'Sunvivapi' is vivid purplish red (near R.H.S. 67B) with eye.
6. The number of flowers per spike of 'Sunvivasmo' is more than that of 'Sunvivapi'.

This new variety of *Verbena* Plant 'Sunvivasamo' was asexually reproduced by the use of cuttings at Yokaichi-shi, Shiga-ken, Japan, and homogeneity and stability thereof were confirmed. The instant plant retains its distinctive characteristics and reproduces true to type in successive generations.

BRIEF DESCRIPTION OF THE PHOTOGRAPHS

The depicted plants had been reproduced by the use of cuttings and were photographed during April 2003 while growing outdoors at an age of approximately 6 months at Yokaichi-shi, Shiga-ken, Japan.

DESCRIPTION OF THE VARIETY

Figure 1:
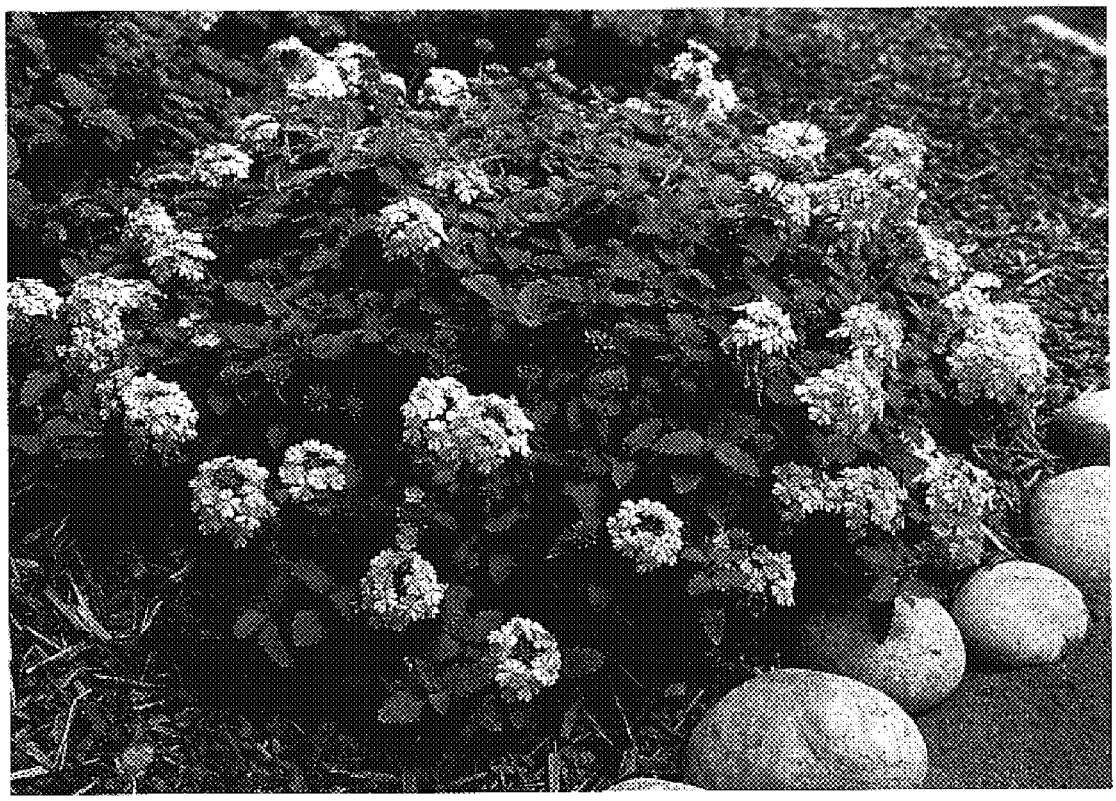
FIG. 1 illustrates a typical plant of the new variety of *Verbena* plant 'Sunvivasamo' growing in the ground.
Figure 2:
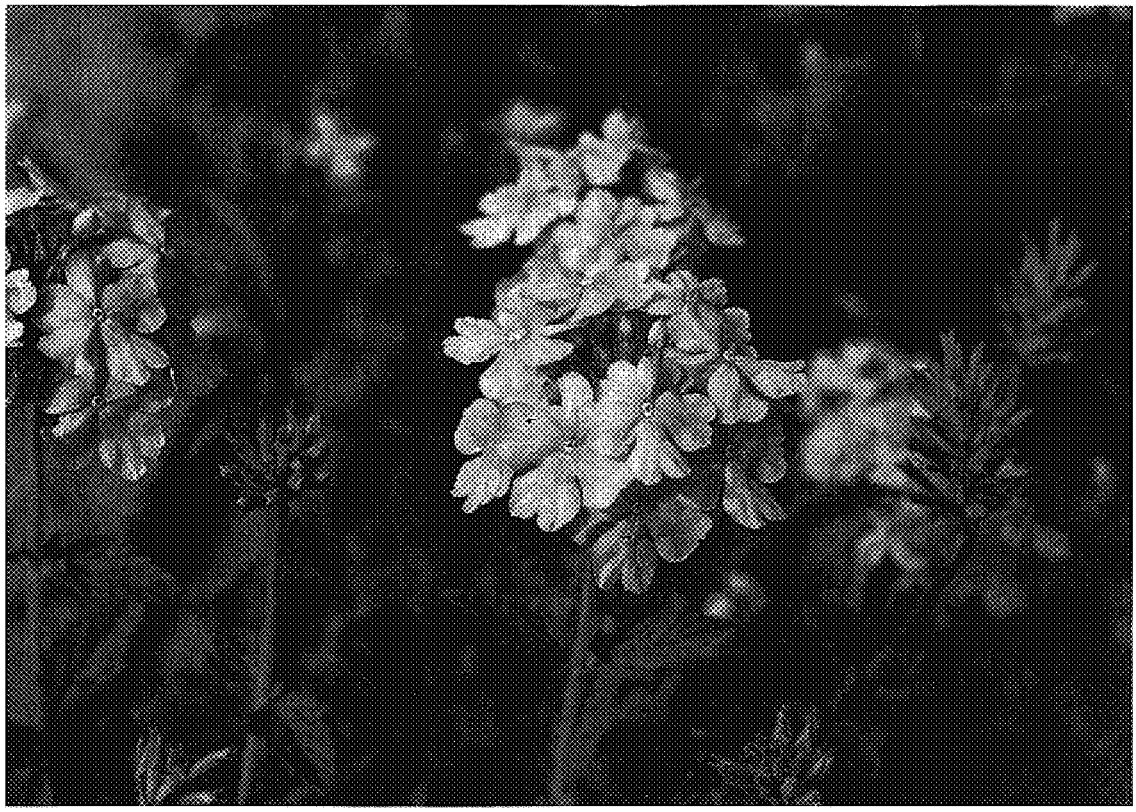
FIG. 2 illustrates a close view of typical foliage and blossoms of the new variety of *Verbena* plant 'Sunvivasamo'.

The botanical characteristics of the new variety of *Verbena* plant named 'Sunvivasamo' are as follows when observed during October at Yokaichi-shi, Shiga-ken, Japan, at an age of 6 months.

Plant:
- *Growth habit.*—Semi-erect.
- *Plant width.*—Approximately 44.5 cm.
- *Plant height.*—Approximately 28.5 cm.

Stem:
- *Diameter.*—Approximately 1.6 mm.
- *Anthocyanin pigmentation.*—Absent.
- *Pubescence.*—Dense.
- *Prickles.*—Absent.
- *Branching.*—Abundant.
- *Subterranean stem.*—Absent.
- *Length of internode.*—Approximately 1.2 cm.

Leaf:
- *Phyllotaxis.*—Opposite.
- *Shape of blade.*—Oblong.
- *Apex shape.*—Obtuse.
- *Base shape.*—Truncate.
- *Margin.*—Serrate.
- *Length.*—Approximately 3.7 cm.
- *Width.*—Approximately 1.9 cm.
- *Color.*—Upper side color is near R.H.S. 138A (Dark olive green); Lower side color is near R.H.S. 147C (moderate yellow green).
- *Pubescence.*—Dense.
- *Petiole.*—Present.

Flower:
- *Shape of cluster.*—Obconical.
- *Cluster length.*—Approximately 3.1–4.0 cm.
- *Cluster diameter.*—Approximately 5.0–5.5 cm.
- *Facing direction.*—Upward.
- *Floret diameter.*—Approximately 1.8–2.0 cm.
- *Floret length.*—Approximately 1.6–1.8 cm.
- *Color of petal.*—Adaxial side: Near R.H.S. 68A (deep purplish pink); Abaxial side: near R.H.S. 68A.
- *Eye color.*—Absent.
- *Variegation.*—Absent.
- *Petal apex.*—Emarginate.
- *Number of petals.*—Generally 5.
- *Calyx length.*—Approximately 1.2–1.5 cm.
- *Calyx shape.*—Tubular. Sepals have an acute apex and are fused at the base.
- *Reproductive organs.*—1 pistil and 4 stamens.
- *Pistil shape.*—Bifid.
- *Anther color.*—Near R.H.S. 1B.
- *Filament color.*—Near R.H.S. 1B.
- *Pollen.*—Present in a moderate quantity; color near R.H.S. 11D.
- *Stigma color.*—Near R.H.S. 4D.
- *Style color.*—Near R.H.S. 144B.
- *Ovaries.*—Commonly four in number.
- *Peduncle diameter.*—Approximately 1.0 mm.
- *Peduncle length.*—Approximately 3.8 cm.
- *Peduncle color.*—Near R.H.S. 137C (Moderate yellow green).
- *Number of flowers per spike.*—Approximately 34.
- *Flowering period.*—April to November in the southern Kanto area, Japan. The plant shape does not change throughout this period. A typical flower commonly lasts 5 to 7 days on the plant when experiencing a temperature of approximately 20° C.
- *Fruit and seed.*—Fruit and seed production has not been observed.

Physiological and ecological characteristics:
- *Winter hardiness.*—USDA Hardiness Zone 4–9 (Grown as perennial).
- *Heat tolerance.*—The plant grows well at temperatures up to at least 35° C.
- *Disease and pest resistance.*—Resistant to powdery mildew. No serious damage by pathogens and pests common to *Verbena* has been observed.

It is claimed:

1. A new and distinct variety of *Verbena* plant named 'Sunvivasamo', substantially as herein illustrated and described.

* * * * *